United States Patent [19]

Michl et al.

[11] Patent Number: 4,787,850

[45] Date of Patent: Nov. 29, 1988

[54] PROCESS FOR PRODUCING DENTURES OF DENTURE PARTS AND STORABLE DENTAL MATERIALS SUITABLE FOR THIS

[75] Inventors: Rudolf J. Michl, Schaan; Peter Wollwage, Mauren; Gerhard Zanghellini, Vaduz, all of Liechtenstein

[73] Assignee: Uexkull & Stolberg, Schaan, Liechtenstein

[21] Appl. No.: 831,459

[22] Filed: Feb. 20, 1986

[30] Foreign Application Priority Data

Feb. 21, 1985 [DE] Fed. Rep. of Germany ....... 3506020

[51] Int. Cl.$^4$ .............................................. A61C 13/00
[52] U.S. Cl. ............................. 433/201.1; 433/202.1; 433/222.1; 523/115; 525/127; 525/131
[58] Field of Search ............... 523/115, 109; 525/131, 525/127; 433/201, 202, 222; 528/75

[56] References Cited

U.S. PATENT DOCUMENTS

| | | | |
|---|---|---|---|
| 3,629,187 | 12/1971 | Waller | 523/115 |
| 3,700,752 | 10/1972 | Hutchinson | 525/454 |
| 4,089,763 | 5/1978 | Dart et al. | 523/115 |
| 4,098,733 | 7/1978 | Oltowski et al. | 525/131 |
| 4,225,696 | 9/1980 | Colpitts et al. | 433/202.1 |
| 4,367,302 | 1/1983 | LeRoy | 528/75 |

OTHER PUBLICATIONS

Polymer, 14, pp. 598–603, Dec. 1973.

*Primary Examiner*—Veronica P. Hoke
*Attorney, Agent, or Firm*—Cushman, Darby & Cushman

[57] ABSTRACT

A process for producing artificial teeth or parts thereof is given, in which a mass of at least one polyfunctional isocyanate, at least one polyol and at least one methacrylate monomer, as well as in each case one catalyst for the polymerization of the methacrylate monomer and for the acceleration of the formation of a urethane is hardened in a first stage to an elastic blank, which can then be cured in a second stage to artificial teeth or parts thereof. A storage-stable dental material for performing the process comprises two components, namely at least one polyfunctional isocyanate as the first component and the remaining constituents as the second component.

11 Claims, No Drawings

PROCESS FOR PRODUCING DENTURES OF DENTURE PARTS AND STORABLE DENTAL MATERIALS SUITABLE FOR THIS

The invention relates to a novel dental material which makes it possible to produce artificial teeth and parts thereof in two stages.

Polymer, 14, pp. 597–603, 1973 discloses producing impactresistant foils by interstitial polymerization, in which e.g. a polyol, a diisocyanate, a tin catalyst, methyl methacrylate and a catalyst for the hot polymerization thereof are mixed together. A polyurethane gel is formed, which can be cured under the action of heat. The impact strength is improved compared with pure polymethyl methacrylate (PMMA).

No reference is made in this publication to the possibility of using such systems for producing dental materials. The given gelling times of 4 to 5 hours and the polymerization time between 3 and 15 hours are completely unsuitable for a usable dental material. In addition, the impact strength is a parameter which is generally of no interest for a dental material.

However, it has surprisingly been found that through the use of urethane/methacrylate systems with at least two suitable catalysts, it is possible to obtain advantageous dental materials, which are also stable in storage in the form of two components. The term dental material is here understood to mean in particular crown and bridge materials, as well as those for producing artificial teeth and inlays.

The subject matter of the invention is a process for producing artificial teeth or parts thereof, such as crowns or inlays with the aid of a curable dental material, which is characterized in that from a mass comprising (a) at least one polyfunctional isocyanate,
(b) at least one polyol,
(c) at least one methacrylate monomer,
(d) a catalyst for the hot, cold or light polymerization of the methacrylate monomer is obtained and
(e) a catalyst for accelerating the formation of a polyurethane from (a) and (b), but which does not accelerate the polymerization of (c)

an elastic blank is produced in a first stage by hardening at ambient temperature and accompanied by shaping, and, optionally following the mechanical finishing thereof, the latter is cured in a second stage to give dentures or parts thereof.

The urethane formed in the dental material can e.g. result from the reaction of polyols with isocyanates in an appropriate molar ratio. Examples of polyols usable according to the invention are ethylene glycol, diethylene glycol, triethylene glycol, 2,2-bis-(4-hydroxyphenyl)-propane, bis-GMA, propylene glycol, 1,3-butanediol, 1,4-butanediol, cyclohexanediol, bis-4,4'-(dihydroxyphenyl)-methane, glycerol, trimethylolethane, trimethylolpropane, pentaerythritol, dipentaerythritol, 1,2,6-hexanetriol, sorbitol, polyethylene glycol, polypropylene glycol, polytetramethylene glycol; polyesters with terminal hydroxy groups, e.g. from adipic acid and diethylene glycol or from maleic anhydride and ethylene glycol; polyhydroxy compounds with ethylene oxide or propylene oxide; partly esterified polyols, e.g. glycerol monomethacrylate and acrylate, pentaerythritol monomethacrylate and acrylate, pentaerythritol dimethacrylate and diacrylate; copolymers of hydroxyethyl methacrylate and methyl methacrylate.

The polyols can be used singly or in a mixture. It is also possible to use prepolymers of diisocyanates or polyisocyanates with the above polyols.

Examples of the isocyanates usable according to the invention are ethylene-diisocyanate, 1,6-hexamethylene-diisocyanate, 2,2,4- and 2,4,4-trimethyl hexamethylene-diisocyanate, 1,6-cyclohexane-diisocyanate, toluylene-diisocyanate, isophorone-diisocyanate, phorone-diisocyanate, 1,5-naphthylene-diisocyanate, 1,3-cylopentylene-diisocyanate, phenylene-diisocyanate, 2,4,6-toluylene-triisocyanate, 4,4',4''-triphenyl methane-triisocyanate, xylylene-diisocyanate, 3,3'-diphenyl methane-diisocyanate, 3,3'-dimethyl-4,4'-diphenyl methane-diisocyanate, 3,3'-dimethyl diphenylene-diisocyanate, 4,4'-diphenylene-diisocyanate, 1-phenoxy-2,4'-phenylene-diisocyanate, 1-tert.butyl-2,4-phenylene-diisocyanate, methylene-bis-4,4'-cyclohexyl-diisocyanate, 1-chloro-2,4-phenylene-diisocyanate, 4,4'-diphenyl ether-diisocyanate, $\Omega,\Omega'$-dipropyl ether-diisocyanate, dicyclohexyl methane-4,4'-diisocyanate and tris-(6-isocyanatohexyl)-biuret.

These isocyanates can be used singly, as a mixture with one another, or as prepolymers. Prepolymers are obtained by reacting with diols or polyols in deficiency. It is also possible to use mixtures of different polyols with different isocyanates.

The polyurethanes are formed in the presence of per se known catalysts, such as are e.g. described in DE-OS No. 27 24 260. In particular, organic tin compounds have proved to be suitable, particular preference being given to dibutyl tin diacetate. The catalysts are normally used in quantities of 0.01 to 10% by weight, based on the total quantity of the dental material. Preferred ranges are 0.1 to 1% by weight, particularly 0.1 to 0.6% by weight.

The dental material must also contain polymerizable vinyl compounds. Particularly suitable are per se known methacrylates in monofunctional or polyfunctional form, which can be used singly or in mixtures. Examples are methyl methacrylate, isobutyl methacrylate, cyclohexyl methacrylate, ethylene glycol dimethacrylate, diethylene glycol dimethacrylate, triethylene glycol dimethacrylate, polyethylene glycol dimethacrylate, butanediol dimethacrylate, hexanediol dimethacrylate, decanediol dimethacrylate, dodecanediol dimethacrylate, bisphenol-A-dimethacrylate, trimethylol propane trimethacrylate, but also bis-GMA, as well as the reaction products of isocyanates, particularly diisocyanates and/or triisocyanates and OH-group-containing methacrylates. Examples of the latter are the reaction products of 1 mol of hexamethylene diisocyanate with 2 mols of 2-hydroxyethyl methacrylate, 1 mol of tris-(6-isocyanatohexyl)-biuret with 3 mols of hydroxyethyl methacrylate, as well as 1 mol of trimethyl hexamethylene diisocyanate and 2 mols of hydroxyethyl methacrylate.

The proportion of these usually long-chain compounds in the dental material ranges between 5 and 60% by weight. When using compounds with several OH-groups, e.g. bis-GMA, the proportion in the dental material can be further increased, because the latter then simultaneously serves as the alcohol component for the urethane reaction. The dental material can then contain 5 to 95% by weight of these compounds.

Catalysts for the hot polymerization of methacrylates are the known peroxides, such as dibenzoyl peroxide, dilauroyl peroxide, tert.-butyl peroctoate or tert.-butyl perbenzoate, but $\alpha,\alpha'$-azodiosobutyronitrile, $\alpha,\alpha'$-azobis-(isobutyroethylester), benzopinacol and 2,2'-dimethyl benzopinacol are also suitable.

It is also possible to use catalysts, which can be activated by radiation. Preference is given to the use of a photosensitizer together with a reducing agent. Examples of photosensitizers are α-diketones such as 9,10-phenanthrene quinone, diacetyl, furil, anisil, 4,4'-dichlorobenzil and 4,4'-dialkoxybenzil. Camphorquinone is used in a preferred manner. Examples of the reducing agents are amines, such as cyanoethyl methyl aniline, dimethyl amino methyl methacrylate, n-butylamine, triethylamine, triethanolamine, N,N-dimethyl aniline or N-methyl diphenyl amine. A particularly preferred combination is camphorquinone and cyanoethyl methyl aniline.

The aforementioned catalysts are used in quantities of 0.01 to 10% by weight, based on the polymerizable material and in particular in quantities of 0.1 to 5% by weight.

It is also appropriate to add so-called drying agents to the dental material. These are preferably zeolites, which can be used in the same concentrations as the fillers. The preferred zeolite content in the dental material is approximately 2 to 20 and particularly 5 to 12% by weight.

As a function of the intended use of the dental material, other inorganic constituents can be present. The fillers can e.g. be constituted by quartz, silica, particularly microfine, pyrogenic, but also precipitated silica, and the per se known glasses. Organic fillers, which are in turn filled with inorganic fillers, can also be used. The fillers are generally used in quantities of 5 to 70, preferably 10 to 50 and particularly 15 to 30% by weight, based on the total dental material weight.

The inorganic constituents of the dental material can be silanized. A suitable coupling agent is e.g γ-methacryloxy propyl trimethoxysilane. The silane quantity used is a function of the filler used.

Other components, e.g. organic polymers can also be added to the dental material. These are preferably produced from the aformentioned polymerizable compounds. It is also possible to use copolymers. Optionally the conventional pigmenting agents, such as e.g. titanium dioxide can be present The urethane formed gives a dental material a rubbery, elastic consistency within a few minutes and this permits further processing, e.g. by cutting or trimming. The consistency undergoes no further change, if the second catalyst used is a catalyst for hot polymerization. The prerequisite is that the two catalysts are chosen in such a way that the catalyst for the urethane formation does not influence the polymerization of the vinyl compounds. This could e.g. be the case if the urethane reaction was catalyzed with an amine. When using catalysts for cold curing or curing under the influence of light, the consistency change of the dental material is dependent on the nature of the catalysts used and their quantity. If desired, after reaching the rubber-elastic phase, the dental material can be cured within a few minutes. However, a cold-curing system can also be marketed in storage-stable manner, if e.g. the components are stored separately and only mixed prior to use.

The invention is preferably used for the production of a temporary or provisional crown and bridge material, but it can also be used with advantage for inlays or as a material for producing artificial teeth. For a temporary crown and bridge material two components are generally mixed together, one component containing the isocyanate and the other component the polyol and the unsaturated vinyl compounds.

A temporary crown and bridge material is used for a temporary fitting, i.e. it is used for bridging the time until the real crown is ready for use. When producing a crown, the dentist firstly takes a silicone impression of the untreated part of the denture or tooth which is to be subsequently given a crown. After taking the impression, the tooth is prepared, i.e. is conically ground. The finished crown will subsequently be located on this conical stump and up to then it must be covered by the temporary fitting.

According to a presently conventional process, the silicone impression is cast with a flowable material, e.g a monomer/polymer mixture or an epimine compound and the entity is placed on the prepared tooth. The pasty phase of the material passes for a short time into a rubber-elastic phase and curing relatively rapidly follows. During the short rubbery or rubber-elastic phase, it is necessary for the dentist to remove the silicone impression, because in the cured state and in the presence of undercuts, it is no longer possible to remove the crown. This is a relatively difficult enterprise, which is not always successful. If the precise time is missed, the temporary crown cures, which means that the dentist must countersink the temporary crown and recommence the process.

The procedure is initially the same with the material according to the invention, but the rubber-elastic phase is permanently maintained. Thus, it is always possible to remove the elastic crown, without the dentist having to match the precise time. In addition, in its elastic phase, the crown is completely adaptable by simply trimming. When the dentist has adapted the temporary crown in its elastic state, it is cured hot or cold and then cemented in as a temporary fitting.

The production of plastic inlays has also hitherto been a very time-consuming laborious operation. If an inlay is to be inserted, then the dentist takes an impression of the prepared cavity and forms one or two plaster models thereof. The cavity in the plaster model is filled with plastic and the latter is polymerized. The thus obtained plastic inlay is removed from the mould and is carefully fitted into a second plaster model by grinding or further working. These operations are performed in a dental laboratory and not by the dentist. Once the laboratory has completed the inlay, the dentist cements it into the cavity of the living tooth.

The material according to the invention can also be used for inlay technology. The two-component material is mixed and introduced into the prepared tooth cavity, where it cures in a rubber-elastic manner. The dentist removes the rubber-elastic inlay from the cavity, carefully fits it and cures it e.g. with light within a few minutes. The inlay can subsequently be cemented into the cavity. This obviates the work in the dental laboratory with plaster models, but it is also conceivable for the accurate fitting of the inlay and the curing to be performed by the laboratory, Artificial teeth are normally made in such a way that a paste of methyl methacrylate and polymethyl methacrylate is prepared, from it are pressed rings, which are placed on the tooth shape, pressed and polymerized. In the case of top quality teeth, this normally takes place in layers, in order to match as closely as possible the appearance of the natural tooth. The pressing of the rings takes place with expensive hydraulic presses, which take up a large amount of space. According to the invention, these rings can be produced by moulding in a ring mould, in which the urethane reaction takes place. After a short time a soft ring is obtained, without expensive equipment being required.

The invention is illustrated by the following examples, in which the quantities are percentages by weight.

EXAMPLES 1 TO 5 (light-hardening materials for temporary crowns)

Examples 1 to 5 relate to a temporary crown and bridge material. The following constituents are mixed together:

TABLE 1

|  | A | B | C | D | E |
|---|---|---|---|---|---|
| Bis-GMA | 68.0 | 61.2 | 34.0 | 61.2 | 34.0 |
| Butanediol dimethacrylate | 17.0 | 15.3 | 8.5 | 15.3 | 8.5 |
| Decanediol dimethacrylate | 2.64 | 2.38 | 1.32 | 2.38 | 1.32 |
| Zeolite (sodium aluminosilicate) | 10.0 | 9.0 | 5.0 | 9.0 | 5.0 |
| Polymer PP 1067* | — | 10.0 | 50.0 | — | — |
| Polymer PP 1068** | — | — | — | 10.0 | 50.0 |
| Dibutyl tin diacetate | 0.5 | 0.45 | 0.25 | 0.45 | 0.25 |
| Camphorquinone | 0.36 | 0.32 | 0.18 | 0.32 | 0.18 |
| Cyanoethyl methyl aniline | 1.50 | 1.35 | 0.75 | 1.35 | 0.75 |

*PP 1067 = Copolymer of 10% HEMA and 90% MMA
**PP 1068 = Copolymer of 20% HEMA and 80% MMA
HEMA = Hydroxyethyl methacrylate
MMA = Methyl methacrylate 2 ml of each of the compositions A to E are mixed with 1 ml of tris-(6-isocyanatohexyl)-biuret (Desmodur N). Polymerization at ambient temperature takes place in approximately 5 minutes, giving an elastic polyurethane compound. Irradiation with a halogen lamp then takes place for 5 minutes, giving a hard end product whose physical values appear in Table 2 (examples 1 to 5).

TABLE 2

| PHYSICAL VALUES | SCUTAN | PROTEMP | CRONSIN | EX. 1 | EX. 2 | EX. 3 | EX. 4 | EX. 5 |
|---|---|---|---|---|---|---|---|---|
| Compressive strength N/mm$^2$ | 143 ± 17 | 127 ± 50 | 373 ± 67 | 385 | 326 ± 24 | 229 ± 22 | 354 ± 51 | 246 ± 25 |
| Elastic limit N/mm$^2$ | 61 ± 8 | 48 ± 12 | 40 ± 6 | 79 | 83 ± 3 | 65 ± 4 | 85 ± 9 | 65 ± 5 |
| Deformation at 200 MPa % | — | — | 65 ± 2 | 43 | 44 ± 0.5 | 50 ± 1 | 44 ± 1 | 50 ± 1 |
| Transverse strength N/mm$^2$ | 51 ± 18 | 59 ± 5 | — | 81 | 75 ± 7 | 56 ± 9 | 56 ± 8 | 71 ± 2 |
| Flexural modulus N/mm$^2$ | 860 ± 400 | 1100 ± 120 | — | 1150 | 2300 ± 190 | 1800 ± 250 | 1800 ± 210 | 2200 ± 140 |
| Extension of the outer fiber % | 4.0 ± 1.1 | 9.7 ± 0.8 | — | 20 | — | 4.6 ± 0.5 | — | 5.2 ± 0.9 |

If no measured values are given, it is because they could not be measured. The transverse strength is determined according to DIN 13922 and the compressive strength according to DIN 13918. The other physical values were also determined on the basis of DIN standards.

For comparison purposes, commercially available materials based on epimine (Scutan), bis-acryl (Protemp) and PEMA (Cronsin) were investigated. Apart from the decisive advantage that the temporary crown according to the invention can be removed at any time and adapted by simply trimming in its rubber-elastic state, examples 1 to 5 also have excellent physical characteristics compared with the prior art materials.

EXAMPLES 6 TO 8 (light, cold and hot-curing dental materials)

The following components were mixed together:

TABLE 3

|  | F | G | H |
|---|---|---|---|
| Bis-GMA | 49.2 | 50.0 | 50.0 |
| Butanediol dimethacrylate | 14.8 | 19.0 | 20.0 |
| Decanediol dimethacrylate | 0.9 | — | — |
| Desmophen 800* | 19.7 | 19.0 | 19.0 |
| Zeolite (sodium alumino-silicate) | 4.9 | 10.0 | 10.0 |

TABLE 3-continued

|  | F | G | H |
|---|---|---|---|
| Polymer PP 1067 (see table 1) | 9.8 | — | — |
| Dibutyl tin diacetate | 0.6 | 0.5 | 0.5 |
| Camphorquinone | 0.1 | — | — |
| Dimethyl-p-toluidine | — | — | 0.5 |
| Benzoyl peroxide (50% in plasticizer) | — | 1.5% | — |

*Highly branched hydroxyl group-containing polyester of adipic acid, phthalic acid and a triol.

The following constituents are mixed together:

EXAMPLE 6

2 parts of F + 1 part of tris-(6-isocyanatohexyl)-biuret. The dental material is cured for 5 minutes at ambient temperature, followed by irradiation for 10 minutes in a light polymerization apparatus.

EXAMPLE 7

2 parts of G + 1 part of tris-(6-isocyanatohexyl]-biuret. The dental material is cured for 5 minutes at ambient temperature (rubber-elastic polyurethane phase). Complete polymerization under water then takes place of the dental material for a further 5 minutes at 120° C. in a pressure polymerization apparatus at 6 bar.

EXAMPLE 8

2 parts of H + 1 part of tris-(6-isocyanatohexyl)-biuret + 0.4 parts of 5% benzoyl peroxide paste in cyclohexyl phthalate. The dental material cures cold. The polyurethane reaction takes place in 5 minutes. The dental material is completely cured at ambient temperature within a further 10 minutes.

TABLE 4

|  | Example 6 | Example 7 | Example 8 |
|---|---|---|---|
| Compressive strength N/mm$^2$ | 400 ± 35 | 459 ± 38 | 352 ± 43 |
| Elastic limit N/mm$^2$ | 73 ± 5 | 111 ± 4 | 81 ± 5 |
| Deformation at 200 MPa % | 49 ± 1.0 | 29 ± 1.0 | 39 ± 1.0 |
| Transverse strength N/mm$^2$ | 56 ± 8 | 108 ± 11 | 65 ± 6 |
| Flexural modulus N/mm$^2$ | 1730 ± 330 | 3200 ± 180 | 2100 ± 160 |
| Extension of the outer fiber % | 8.5 ± 1.5 | 4.8 ± 1.2 | 7.5 ± 2.2 |

EXAMPLE 9

The following components are mixed together:

|  | I |
|---|---|
| Methyl methacrylate | 43.5 |
| Ethylene glycol dimethacrylate | 3.5 |
| Desmophen 800 (see table 3) | 46.5 |
| Zeolite (sodium alumino silicate) | 5 |
| 50% benzoyl peroxide | 1 |

| | I |
|---|---|
| Dibutyl tin diacetate | 0.5 |

2 parts of I are mixed with 1 part of tris-(6-isocyanatohexyl)-biuret. The mixture is mouldable and suitable for moulding rings for the production of dentures.

A toothbrush abrasion test is performed. A chalk suspension is applied to a lined rotary disk (80 r.p.m.). A test piece is produced from the material according to example 9 (4 mm thick, diameter 15 mm). The test piece is produced in a pressure polymerization apparatus for 15 minutes, at 120° C. and 6 bar. The test piece is loaded with 400 g and placed on the rotary disk. The weight loss after 2 hours is measured on the test piece and a test piece made from polymethyl methacrylate. The polymethyl methacrylate weight loss is considered equal to 100%. The following results are obtained:

| PMMA | 100% by weight |
|---|---|
| Dental material according to example 9 | 9.3% by weight |

From the material it is possible to produce artificial teeth having a good abrasion resistance, the rings being produced by moulding in moulds. There is no need for the hydraulic pressures conventionally used for pressing rings.

We claim:

1. A two stage process for producing artificial teeth or crowns, inlays or other tooth parts using a curable dental material, in which process the first stage comprises producing a rubbery elastic blank by hardening at ambient temperature a composition comprising
   (a) at least one polyfunctional isocyanate,
   (b) at least one polyol,
   (c) at least one methacrylate monomer having at least two hydroxyl groups,
   (d) a catalyst for the heat or light initiated polymerization of the methacrylate monomer, and
   (e) a catalyst for accelerating the formation of a polyurethane from (a), (b) and (c) which does not catalyze the radical polymerization of (c), shaping and mechanically finishing the blank, and the second stage comprises curing the shaped rubbery composition to provide said hard artificial teeth or parts thereof.

2. Process according to claim 1, wherein a composition is used in which constituents (a), (b) and (c) together contain constituents (a) and (b) in a quantity of from 40 to 95% by weight and constituent (c) in a quantity of from 5 to 60% by weight.

3. Process according to claim 1, wherein a composition is used in which constituents (b) and (c) together contain at least one methacrylate having at least two hydroxyl groups in a quantity of 5 to 100% by weight.

4. Process according to claim 1, wherein a composition is used which contains, as constituents (a) and (b), a prepolymer formed from a stoichiometric excess of polyfunctional isocyanates with respect to the polyol content thereof, and as a methacrylate monomer (c) a compound containing at least two hydroxy groups.

5. Process according to claim 1, wherein catalyst (d) is a combination of an alpha-diketone and an amine reducing agent.

6. Process according to claim 1, wherein catalyst (e) is an organic tin compound.

7. A storable dental fabrication material for producing artificial teeth or crowns, inlays or other tooth parts comprising a first separate component comprising
   (a) at least one polyfunctional isocyanate, and a second separate component comprising
   (b) at least one polyol,
   (c) at least one methacrylate monomer having at least two hydroxyl groups,
   (d) a catalyst for the heat or light initiated polymerization of the methacrylate monomer, and
   (e) a catalyst for acceleration of the formation of a polyurethane from constituents (a), (b) and (c) which does not catalyze the polymerization of the methacrylate monomer (c).

8. A dental material according to claim 7, wherein the combined first and secnd components are composed of constituents (a) and (b) in a quantity of 40 to 95% by weight and constituent (c) in a quantity of 5 to 60% by weight, based on the combined weight of the polymerizable organic constituents (a), (b) and (c).

9. Dental material according to claim 7, wherein constituents (b) and (c) together contain at least one methacrylate having at least two hydroxyl groups in a quantity of 5 to 100% by weight.

10. Dental material according to claim 7, wherein catalyst (d) is a combination of an alpha-diketone and an amine reducing agent.

11. Dental material according to claim 7, wherein catalyst (e) is an organic tin compound.

* * * * *

UNITED STATES PATENT AND TRADEMARK OFFICE
CERTIFICATE OF CORRECTION

PATENT NO. : 4,787,850

DATED : November 29, 1988

INVENTOR(S) : Michl et al

It is certified that error appears in the above-identified patent and that said Letters Patent is hereby corrected as shown below:

On the Title Page, change the Assignee information to read:

--[73] Assignee: Etablissement Dentaire Ivoclar, Schaan/Liechtenstein--

Signed and Sealed this

Eighteenth Day of April, 1989

Attest:

DONALD J. QUIGG

*Attesting Officer*

*Commissioner of Patents and Trademarks*